(12) United States Patent
Fisher et al.

(10) Patent No.: US 10,399,895 B2
(45) Date of Patent: Sep. 3, 2019

(54) BISMUTH-INDIUM ALLOY FOR LIQUID-TIGHT BONDING OF OPTICAL WINDOWS

(71) Applicant: PIKE Technologies of Wisconsin, Inc., Madison, WI (US)

(72) Inventors: Alec Cameron Fisher, Madison, WI (US); Kent Gundlach, Madison, WI (US)

(73) Assignee: Pike Technologies of Wisconsin, Inc., Madison, WI (US)

( * ) Notice: Subject to any disclaimer, the term of this patent is extended or adjusted under 35 U.S.C. 154(b) by 0 days.

(21) Appl. No.: 16/218,895

(22) Filed: Dec. 13, 2018

(65) Prior Publication Data

US 2019/0177218 A1 Jun. 13, 2019

Related U.S. Application Data

(60) Provisional application No. 62/598,058, filed on Dec. 13, 2017.

(51) Int. Cl.
*G01N 1/10* (2006.01)
*C03C 27/08* (2006.01)
*C22C 28/00* (2006.01)
*G01N 21/09* (2006.01)
*G01N 21/03* (2006.01)

(52) U.S. Cl.
CPC .............. *C03C 27/08* (2013.01); *C22C 28/00* (2013.01); *G01N 21/09* (2013.01); *G01N 2021/0389* (2013.01); *G01N 2201/0227* (2013.01); *G01N 2201/068* (2013.01)

(58) Field of Classification Search
CPC ...... G01N 30/74; G01N 21/031; G01N 21/05; G01N 21/03; G01N 21/0303
USPC ....................................................... 356/246
See application file for complete search history.

(56) References Cited

U.S. PATENT DOCUMENTS

| 4,005,920 A | 2/1977 | Wimmer |
| 4,039,877 A | 8/1977 | Wimmer |
| 2012/0250023 A1* | 10/2012 | Bartlett ................. G01N 21/05 356/440 |

OTHER PUBLICATIONS

Okamoto, Bismuth-Indium Binary Phase Diagram, Binary Alloy Phase Diagrams, (1990) ASM International, USA, II Ed.

* cited by examiner

*Primary Examiner* — Md M Rahman
(74) *Attorney, Agent, or Firm* — Quarles & Brady LLP

(57) ABSTRACT

Disclosed herein are seals for liquid-tight bonding of an optical window comprising a Bi—In alloy. Also disclosed are optical cells comprising the Bi—In alloy seals to provide a liquid-tight seal between a cell housing and a drilled optical window.

16 Claims, 4 Drawing Sheets

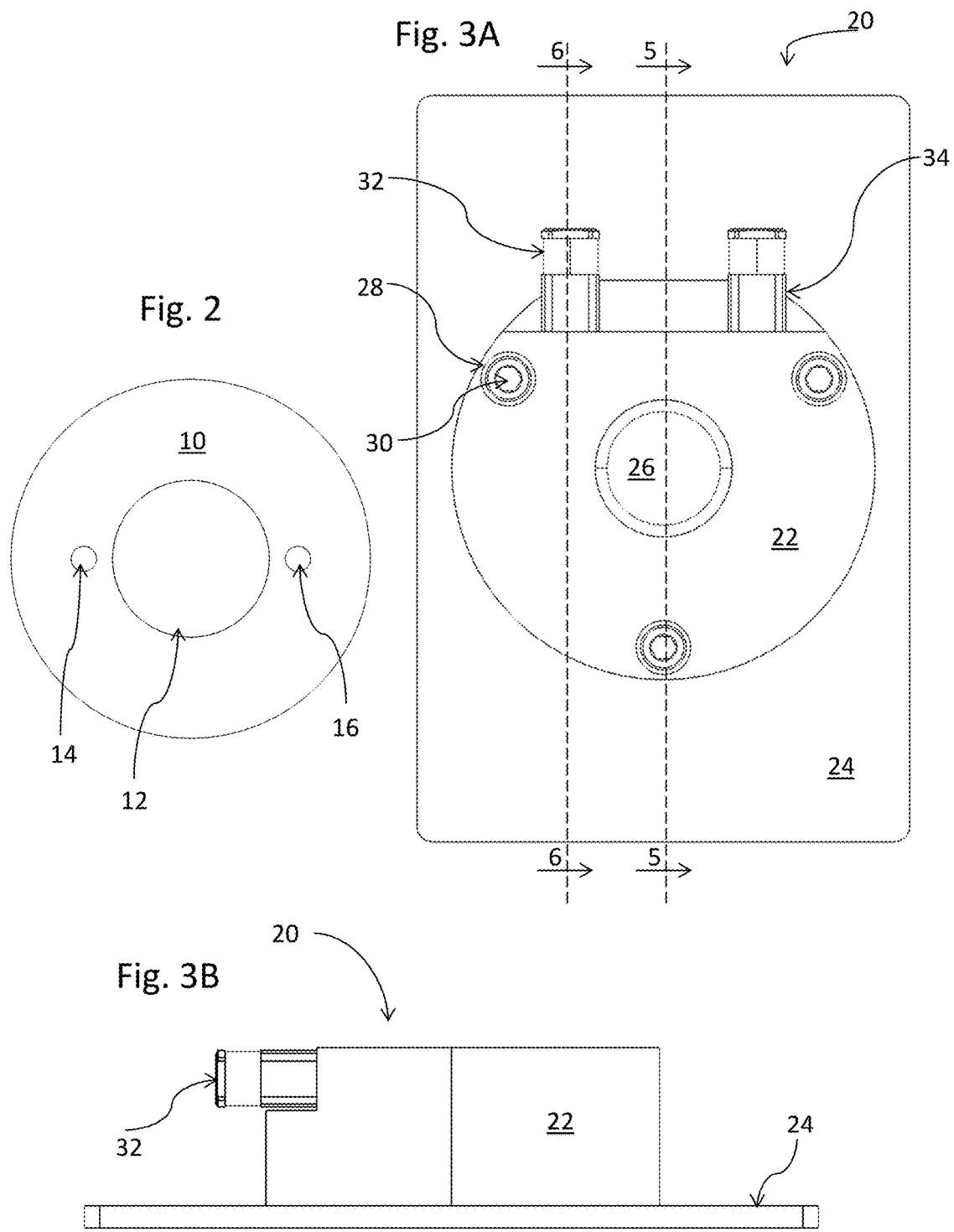

BISMUTH-INDIUM ALLOY FOR LIQUID-TIGHT BONDING OF OPTICAL WINDOWS

CROSS-REFERENCE TO RELATED PATENT APPLICATIONS

The present application claims the benefit of priority of United States Provisional Patent Application No. 62/598,058, filed on Dec. 13, 2017, the contents of which are incorporated herein by reference in its entirety.

FIELD OF INVENTION

The present disclosure is directed to liquid-tight binding of optical windows. More particularly, the present disclosure is directed to liquid-tight binding of optical windows utilizing Bi—In alloy seals.

BACKGROUND

Optical cells typically comprise two optical windows, one with inlet and outlet holes, separated by a spacer held together by a housing. In order for the cell to be liquid tight, there are two types of interfaces that need to be sealed: the interfaces between the windows and the spacer and the interface between the drilled window and the housing. Preferably the seals should be chemically resistant, which precludes the use of typical polymer adhesives. One solution for sealing the interface between the drilled window and the housing has been Pb—Hg seals. However, Pb—Hg seals are not chemically resistant and can leach Pb and/or Hg. As a result, there exists a need for new seals capable of providing liquid-tight seals that are chemically resistant.

BRIEF SUMMARY OF THE INVENTION

Disclosed herein are seals comprising a Bi—In alloy for liquid-tight bonding of an optical window. The seals are chemically resistant to a wide variety of chemicals and solvent, i.e., resistant to chemical attack or solvent reaction, including resistance to swelling or softening of the material, leaching of seal material, or chemical modification of the surface. In some embodiments, the Bi—In alloy is a eutectic composition. In some embodiments, the Bi—In alloy comprises about 66.0-67.0% In by weight and/or about 33.0-34.0% Bi by weight.

Also disclosed herein are optical cells comprising: a cell housing, the cell housing comprising an aperture, an inlet port and an outlet port; a seal comprising a Bi—In alloy and having an aperture, an inlet conduit, and an outlet conduit; a drilled optical window having an inlet and an outlet; a chemically resistant spacer having an aperture; and an undrilled optical window. The seals are configured to form a liquid-tight seal between the drilled optical window and the cell housing. The seals also allow for introduction of a sample via the inlet port of the cell housing, the inlet conduit of the seal, and the inlet of the drilled optical window into a chamber formed from the drilled optical window, the spacer, and the undrilled optical window and elimination of the sample via the outlet port of the cell housing, the outlet conduit of the seal, and the outlet of the drilled optical window from the chamber. The aperture of the cell housing, the aperture of the seal, and the aperture of the spacer allows for optical measurement of the sample within the chamber between the drilled optical window and the undrilled optical window. The cell may further comprise a compressible gasket and/or a second spacer interposed between a mounting plate and the undrilled window.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 2 shows an exemplary seal.
FIG. 3A shows an optical cell.
FIG. 3B shows the optical cell of FIG. 3A from the side perspective.

DETAILED DESCRIPTION OF THE INVENTION

The present disclosure is directed to Bi—In alloy seals for liquid-tight bonding of optical windows and cells. The Bi—In alloy seal acts as an adhesive agent to bond optical materials to structural materials. Bi—In alloy seals have a low melting point and high malleability similar to other seals, but also provide for chemical resistance.

Figure 1:
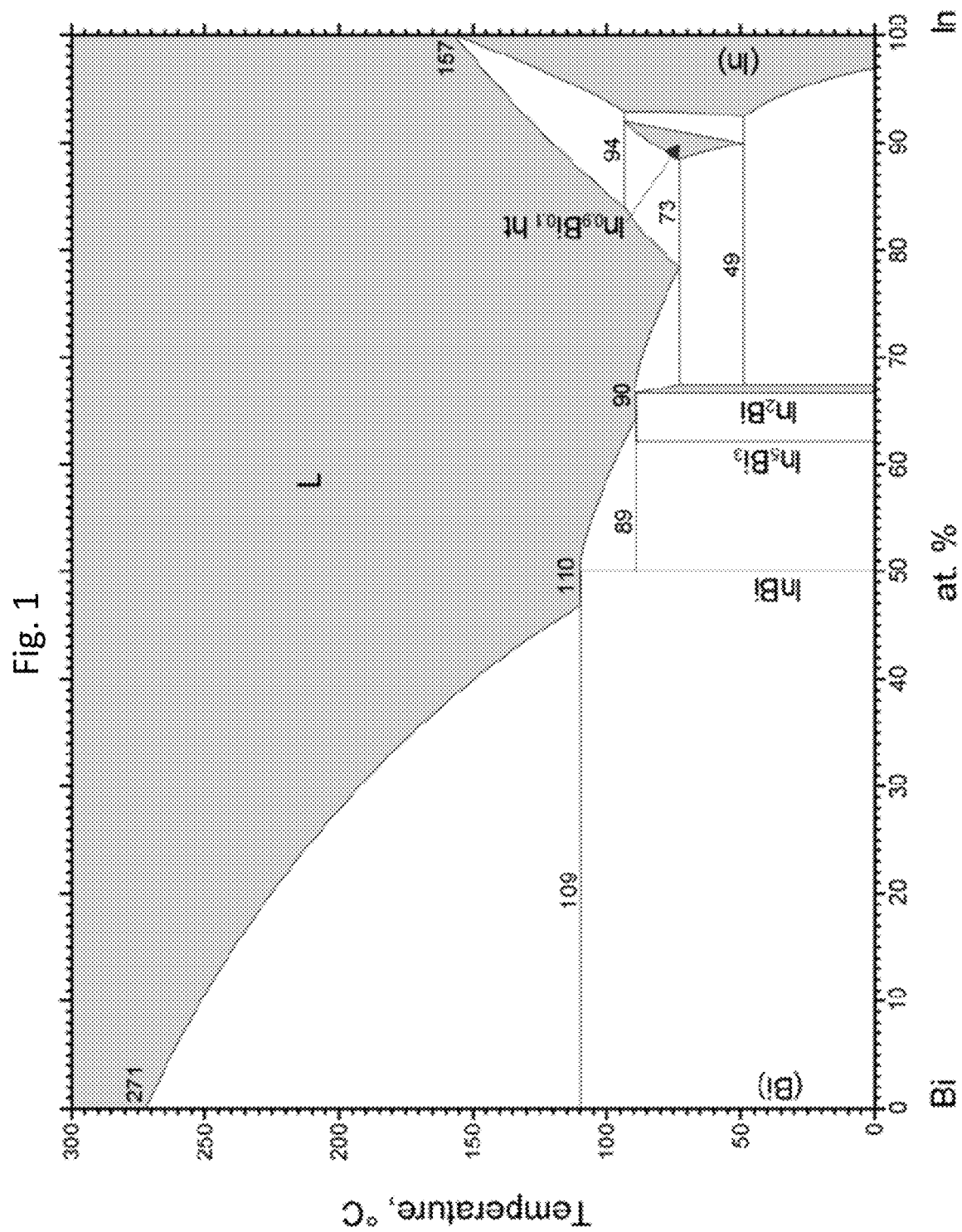
FIG. 1 phase diagram for a binary Bi—In alloy.

The seals of the present invention comprise Bi and In. The relative proportion of Bi and In can be in any suitable proportion. In some embodiments, the seal comprises a Bi—In alloy. Suitably the Bi—In alloy is a eutectic composition. Several eutectic compositions comprising Bi and In are known for binary Bi—In alloys (FIG. 1). H. Okamoto, Bismuth-Indium Binary Phase Diagramm in Binary Alloy Phase Diagrams, II Ed., Ed. T. B. Massalsaki et al. (1990). The Bi—In alloy may comprise between about 66.0% to about 67.0%, about 66.5% to about 68.9%, or about 66.6% to about 66.8% In by weight. The Bi—In alloy may comprise between about 33.0% to about 34.0%, about 33.1% to about 33.5%, or about 33.2% to about 33.4% Bi by weight. In some embodiments, the Bi—In alloy comprises between about 66.0% to about 67.0%, about 66.5% to about 68.9%, or about 66.6% to about 66.8% In by weight and between about 33.0% to about 34.0%, about 33.1% to about 33.5%, or about 33.2% to about 33.4% Bi by weight.

Alternatively, the Bi—In alloy may be described by the atomic percentage (at %) of the elements. The Bi—In may comprises about 77.9 at % to about 80.9 at %, about 78.3 at % to about 78.6 at %, or about 78.5 at % to about 78.6 at % In. The Bi—In may comprises about 19.1 at % to about 22.1 at %, about 21.4 at % to about 21.7 at %, or about 21.4 at % to about 21.6 at % Bi. In some embodiments, the Bi—In alloy comprises about 77.9 at % to about 80.9 at %, about 78.3 at % to about 78.6 at %, or about 78.5 at % to about 78.6 at % In and 19.1 at % to about 22.1 at %, about 21.4 at % to about 21.7 at %, or about 21.4 at % to about 21.6 at % Bi.

Additional elements may be present in the Bi—In alloy, provided that additional elements allow the alloy to maintain a low melting point, high malleability, and chemical resistance. In some embodiments, the Bi—In alloy consists essentially of Bi—In. Suitably the Bi—In alloy consists essentially of Bi and In with less than 2% by weight of additional elements. Suitably, the Bi—In alloy comprises less than 1.5%, 1.0%, 0.5%, or 0.2% by weight of additional elements. Suitably, the Bi—In alloy may consist essentially of about 66.0% to about 67.0%, about 66.5% to about 68.9%, or about 66.6% to about 66.8% In by weight and between about 33.0% to about 34.0%, about 33.1% to about 33.5%, or about 33.2% to about 33.4% Bi by weight.

The seal may comprise an aperture and at least one conduit transverse to faces of the seal. The aperture is suitably configured to allow for incident electromagnetic radiation or a transmitted signal to pass without substantial disruption to the electromagnetic radiation or the transmitted signal. As used herein, "substantial disruption" means that a characteristic of the electromagnetic radiation or the transmitted signal is altered to a sufficient extent as to compromise spectroscopic analysis of a sample. Characteristics of the electromagnetic radiation or the transmitted signal may include, without limitation, wavelength or frequency, intensity, power, profile, phase, bandwidth, coherence, directionality, or divergence. The aperture may be formed by the absence of material, e.g., a hole or gap, or may be formed from a material capable of allowing the electromagnetic radiation or the transmitted signal. The conduit is suitably configured to allow for fluid communication between different components such as structural and optical components.

FIG. 2 illustrates an exemplary seal of the present invention. The seal 10 comprises an inner edge forming an aperture 12 and conduits 14 and 16. The seal 10 as well as aperture 12 and conduits 14 and 16 have a round or circular cross-section but they need not be configured to have round or circular cross-sections. Each of the seal, aperture, and conduits may be independently configured in any suitable form, e.g., rectangular, square, or hexagonal.

The sealing properties may be improved by having substantially flat faces and/or faces separated by a substantially uniform thickness. In some embodiments, the seal comprises a mean thickness between about 0.0001 to about 0.001, about 0.0002 to about 0.0009, about 0.0003 to about 0.0008, 0.0004 to about 0.0007, or about 0.0005 inches between the faces of the seal.

Seals may be prepared by any suitable method. One exemplary method for preparing the seals comprises running a sheet of the Bi—In alloy between rollers a multiplicity of times and successively reducing the separation between the rollers. Once the desired thickness is obtained, the sheet of the Bi—In alloy may be cut or stamped to prepare a seal having an aperture, a conduit, and suitably sized and shaped to be used with an optical cell.

An exemplary optical cell 20 using is shown in FIGS. 2A and 2B. The seal (not shown) is positioned between housing 22 and a mounting plate 24. The cell housing 22 may be made of any suitable material and shape to provide structural integrity to the optical cell, protect delicate optical components, and/or provide a mechanism for compressing the optical components to provide liquid-tight seals. The housing comprises a housing aperture 26 allows for unobstructed optical measurement of a liquid sample within the optical cell. Housing ports 32 and 34 allows for introduction and/or evacuation of the sample from optical cell 20. The mounting plate 24 made of any suitable material and shape to provide structural integrity to the optical cell, protect delicate optical components, and/or provide a mechanism for compressing the optical components to provide liquid-tight seals. The components of the optical cell may be secured together via screws 30 and screw holes 28. Suitably the screws 30 may be used to apply a compressive force onto the internal components to improve liquid-tight sealing between the interfaces of the components.

In some embodiments, one of the ports may be used for introduction of a sample and the other for evacuation of a sample from within the optical cell. For example, port 32 may be an inlet port configured to allow for introduction of a sample into the optical cell and the port 34 may be an outlet port configured to allow for evacuation of the sample from the optical cell. In some embodiments, ports 32 and 34 may comprise press-fit Luer fittings, threaded Luer fittings, compression fittings or another fitting for a leak-free connection.

Figure 4A:
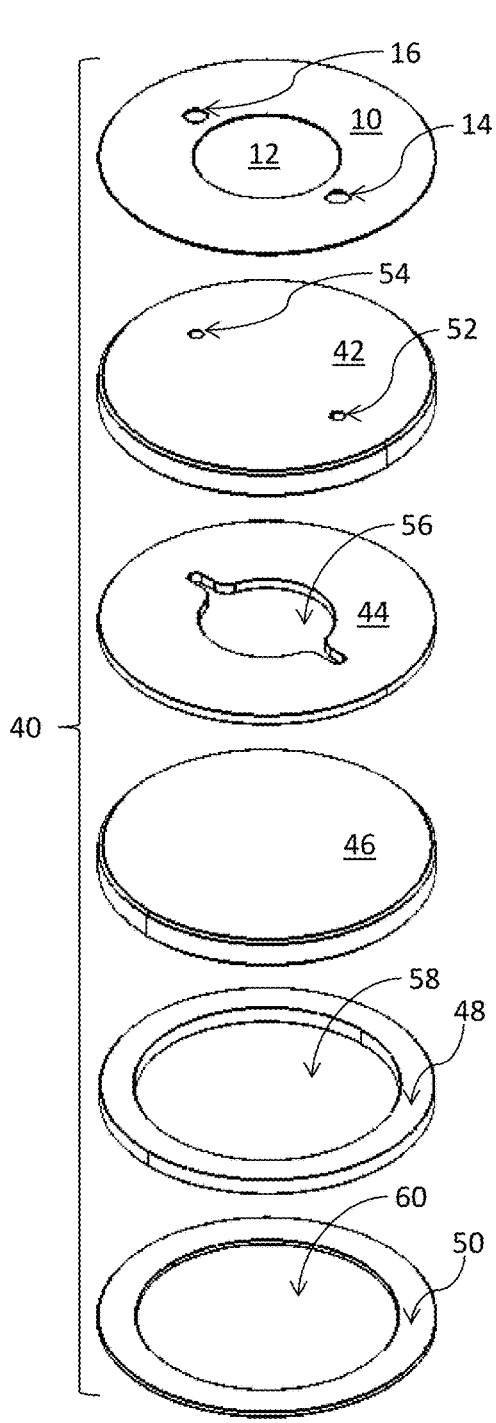
FIG. 4A shows an exploded view of an internal component stack.
Figure 4B:
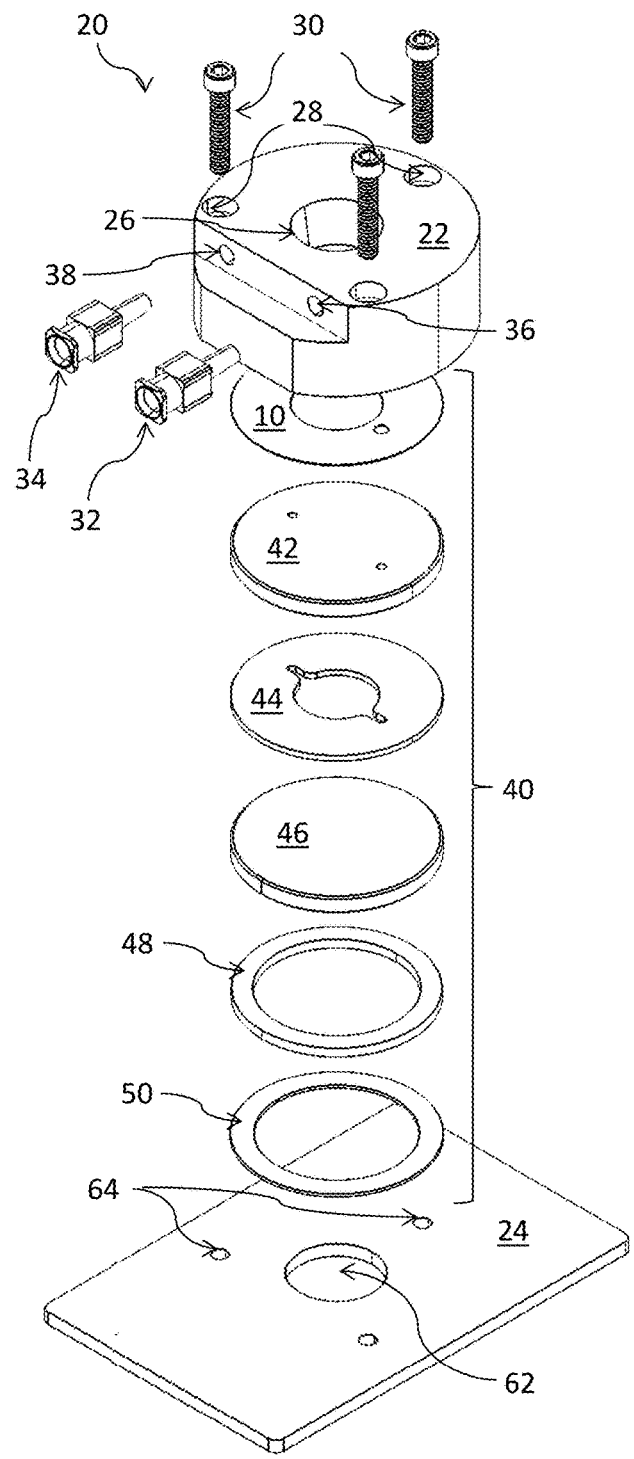
FIG. 4B shows an exploded view of the optical cell of FIG. 3A.

FIGS. 4A and 4B illustrate exploded views of an internal component stack 40 and the optical cell 20, including the internal component stack 40, respectively. The internal component stack 40 comprises the seal 10, a drilled optical window 42, spacer 44, and an undrilled optical window 46. When assembled, the drilled optical window 42, the spacer 44, and the undrilled optical window 46 form a chamber for housing a liquid sample.

The drilled window 42 may comprise an inlet 52 and an outlet 54. The inlet 52 allows for the introduction of a sample into a chamber formed from the drilled window 42, a spacer 44, and an undrilled window 46. The drilled window 42 may also be made of any suitable material to allow for optical measurements to be taken of a sample. In some embodiments, the optical measurements are taken in the ultraviolet (UV), visible, near-infrared (near-IR), mid-IR, or far-IR. Preferably the drilled window 42 is transparent in the spectral region of interest. The drilled window 42 may comprise an amorphous material transmitting infrared radiation, polyethylene, $Al_2O_3$, $BaF_2$, $CaF_2$, CdTe, CsI, GaAs, Ge, KBr, KCl, LiF, $MgF_2$, NaCl, Si, $SiO_2$, thallium-bromoiodide (KRS-5), ZnS, ZnSe, or any other suitable material. The drilled window 42 and the undrilled window 46 may be made of the same material but need not be.

The spacer 44 may be composed of any suitable material that allows for the drilled window 42 and the undrilled window 46 to be maintained at the desired separation. In some embodiments, the spacer 44 has a Shore hardness between about 40 D to about 70 D, about 45 D to about 65 D, or about 50 D to about 60 D. The spacer 44 may also comprise of a chemically resistant material, such as a chemically-resistant polymer. As used herein, "chemically-resistant" means that material will not react with a sample within the chamber or, if there is a reaction, the reaction will be of such minor extent as not to interfere with the analysis of the sample within the chamber. An exemplary polymer having chemical resistance and suitable hardness to maintain the desired separation between the windows is polytetrafluoroethylene. The spacer 44 may have an aperture 56 which can be aligned with the seal aperture 12 and housing aperture 26, forming an optical path transverse to the drilled optical window and the undrilled optical window. Suitably, the optical path allows for an unobstructed optical measurement of a sample and/or without substantial disruption to incident electromagnetic radiation or a transmitted signal.

The cell may comprise a compressible gasket 48 interposed between the undrilled window 46 and the mounting plate 24. The compressible gasket allows for compressive forces to be evenly distributed and to reduce the likelihood that any compressive forces are too great or result in component failure. In some embodiments, the gasket 48 has a Shore hardness between about 30 A to about 80 A, about 40 A to about 70 A, or about 45 A to 65 A. The gasket 48 may have any suitable thickness. In certain embodiments, the gasket 48 has a thickness between about 1/32 and about 1/4, or about 1/16 to about 1/8 of an inch. The gasket may be made of any suitable material and in certain embodiments silicone. The gasket 48 may comprise an aperture 58, which can align with any of the apertures of the cell's components.

To minimize the bending stress on the optical windows 42 and 46 and reduce the likelihood to stress failure, the area of contact between undrilled window 46 and the compression gasket 48 should opposed by the area of contact between the spacer 44 and undrilled window 46. In other words, the compression gasket 48 should not extend inwardly past the inner edge of spacer 44 or overlap aperture 56 as this may stress optical window 46, leading to failure. This issue is mitigated by limiting the area where compression gasket 48 contacts window 46 to areas that are supported by spacer 44 on the opposite side.

The internal component stack 40 may comprise a second spacer 50 interposed between the undrilled window 46 and the mounting plate 24. The spacer 50 may have an aperture 60 which can align with any of the apertures of the cell's components. In some embodiments, the spacers 44 and 50 may be the same size and shape and/or comprised of the same material. In other embodiments, spacers 44 and 50 may be of different size or shape and/or comprised of different materials.

The mounting plate 24 may comprise an aperture 62, which can align with any of the apertures of the cell's components. The mounting plate 24 may also comprise screw holes 64 where screws 30 can be used to join the cell components and/or provide compressive force to the interior components to provide liquid-tight seals.

Figure 5:
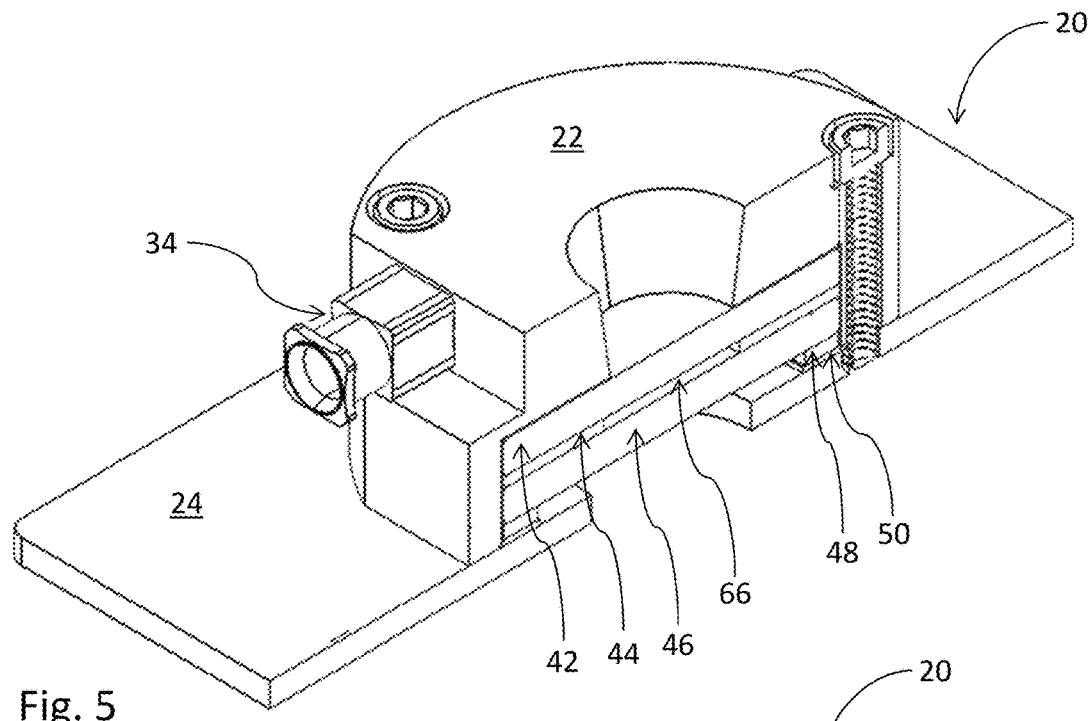
FIG. 5 shows a cross-sectional view of the optical cell of FIG. 3A along line 5.
Figure 6:
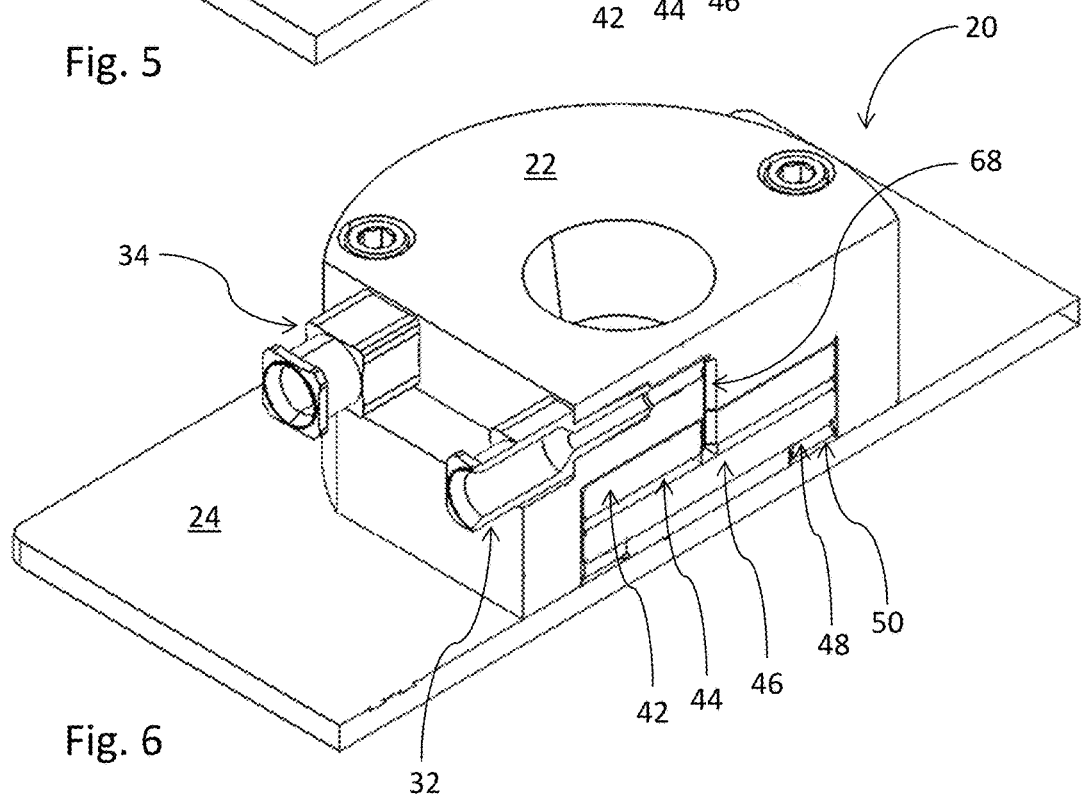
FIG. 6 shows a cross-sectional view of the optical cell of FIG. 3A along line 6.

FIGS. 5 and 6 provide cross-sectional views of the of the optical cell 20 illustrated in FIG. 3A along dashed lines 5 and 6, respectively. FIG. 5 illustrates the chamber 66 formed from the drilled optical window 42, the spacer 44, and the undrilled optical window 46 form a chamber for housing a liquid sample. The seal is present between the cell housing 22 and the drilled optical window 42 in FIG. 5, but the relative thicknesses of the components makes it difficult to distinguish the seal and is not labeled. FIG. 5 also illustrates the alignment of the apertures of the cell housing 22, seal 10, spacers 44 and 50, compressible gasket 48, and mounting plate 24 forming an optical path transverse to the drilled optical window and the undrilled optical window.

FIG. 6 illustrates the connections allowing for liquid communication between the components of the optical cell. As an example, a sample introduced into the chamber of optical cell 20 via port 32 may flow through an internal conduit 68 within the cell housing 22, a seal conduit, and the inlet of the drilled window 42. The seal is present between the cell housing 22 and the drilled optical window 42 in FIG. 5, but the relative thicknesses of the components makes it difficult to distinguish the seal and is not labeled. Alternatively, the sample may be evacuated from the chamber of the optical cell 20 via port 32 by flowing from the chamber through an outlet of the drilled window 42, a conduit of the of the seal, and an internal conduit 68 within the cell housing 22.

The seal and optical cells disclosed herein may be used to perform a number of different spectroscopic analyses, including transmission or absorption analyses such as Fourier-transform infrared spectroscopies. Methods for the spectroscopic analysis of a sample may comprise providing any of the optical cells described herein and introducing a liquid sample into a chamber. The sample may be irradiated with electromagnetic radiation, suitably ultraviolet (UV), visible, near-infrared (near-IR), mid-IR, or far-IR. The electromagnetic radiation may be provided by any suitable source of radiation, including narrowband, e.g., a laser, or broadband radiation sources, e.g., a lamp, incandescent wire, or glower. Suitably a signal will be detected. Suitably the signal with has one or more detectable characteristic of the electromagnetic radiation such as wavelength or frequency, intensity, power, profile, phase, bandwidth, coherence, directionality, or divergence indicative of the interaction of electromagnetic radiation with the sample. Suitably the signal may be detected with a thermal, pyroelectric, or photoconducting detector. Depending on the analysis of interest, a sample may be introduced and evacuated in a batch-wise manner. Alternatively, a sample may be introduced and evacuated continuously.

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. An optical cell comprising:
   (a) a cell housing, the cell housing comprising a housing aperture, an inlet port, and an outlet port;
   (b) a seal, the seal comprising a seal aperture, an inlet conduit, and an outlet conduit, wherein the seal comprises a Bi—In alloy;
   c) a drilled optical window, the drilled optical window comprising an inlet and an outlet;
   (d) a spacer, the spacer comprising a spacer aperture; and
   (e) an undrilled optical window,
   wherein the drilled optical window, the spacer, and the undrilled optical window form a chamber,
   wherein the housing aperture, the seal aperture, and the spacer aperture are aligned and form an optical path transverse to the drilled optical window and the undrilled optical window;
   wherein the seal is configured to form a liquid-tight seal between the housing and the drilled optical window and allow fluid communication between the inlet port and inlet via the inlet conduit and the outlet port and the outlet via the outlet conduit.

2. The cell of claim 1, wherein the Bi—In alloy comprises 66.0-67.0% In by weight and/or 33.0-34.0% Bi by weight.

3. The cell of claim 1, wherein the Bi—In alloy consists essentially of 66.0-67.0% In by weight and 33.0-34.0% Bi by weight.

4. The cell of claim 1 further comprising a mounting plate, the mounting plate comprising an aperture aligned with the housing aperture, the seal aperture, and the spacer aperture.

5. The cell of claim 4 further comprising a compressible gasket interposed between the undrilled optical window and the mounting plate.

6. The cell of claim 5, wherein the gasket has a Shore hardness between about 30 A to about 80 A.

7. The cell of claim 6, wherein the spacer has a greater hardness than the gasket.

8. The cell of claim 7, wherein the spacer has a Shore hardness between about 40 D to about 70 D.

9. The cell of 8 further comprising a second spacer interposed between the undrilled optical window and the mounting plate.

10. The cell of claim 1, wherein the inlet port and/or the outlet port comprises a Luer fitting.

11. The cell of claim 1, wherein the drilled window and/or the undrilled window comprises an amorphous material transmitting infrared radiation, polyethylene, $Al_2O_3$, $BaF_2$, $CaF_2$, CdTe, CsI, GaAs, Ge, KBr, KCl, LiF, $MgF_2$, NaCl, Si, $SiO_2$, thallium-bromoiodide (KRS-5), ZnS, or ZnSe.

12. A method for the spectroscopic analysis of a sample, the method comprising:
    (a) providing the optical cell of claim 1;
    (b) introducing a liquid sample into the chamber of the optical cell;
    (c) irradiating the sample with electromagnetic radiation; and
    (d) detecting a signal.

13. The method of claim 12 further comprising (e) evacuating the sample from the chamber.

14. The method of claim 12, wherein the Bi—In alloy comprises 66.0-67.0% In by weight and/or 33.0-34.0% Bi by weight.

15. The method of claim 12, wherein the Bi—In alloy consists essentially of 66.0-67.0% In by weight and 33.0-34.0% Bi by weight.

16. The method of claim 12, wherein the cell further comprises:
    a mounting plate, the mounting plate comprising an aperture aligned with the housing aperture, the seal aperture, and the spacer aperture; and
    a compressible gasket interposed between the undrilled optical window and the mounting plate.

* * * * *